(12) United States Patent
Levine

(10) Patent No.: US 12,250,960 B2
(45) Date of Patent: Mar. 18, 2025

(54) COMPOSITION AND METHOD EFFECTIVE FOR INDUCTION OF REMISSION OF CROHN'S DISEASE

(71) Applicant: CREATIVE MEDICAL DIETS LTD., Mazkeret Batya (IL)

(72) Inventor: Arie Levine, Mazkeret Batia (IL)

(73) Assignee: CREATIVE MEDICAL DIETS LTD., Mazkeret Batya (IL)

( * ) Notice: Subject to any disclaimer, the term of this patent is extended or adjusted under 35 U.S.C. 154(b) by 1065 days.

(21) Appl. No.: 17/076,386

(22) Filed: Oct. 21, 2020

(65) Prior Publication Data

US 2021/0030047 A1   Feb. 4, 2021

Related U.S. Application Data

(63) Continuation of application No. 15/307,008, filed as application No. PCT/IL2015/050028 on Jan. 7, 2015, now abandoned.

(60) Provisional application No. 61/928,024, filed on Jan. 16, 2014.

(51) Int. Cl.
*A23L 33/00* (2016.01)
*A23L 35/00* (2016.01)
*A61K 36/00* (2006.01)

(52) U.S. Cl.
CPC .............. *A23L 33/40* (2016.08); *A23L 33/30* (2016.08); *A23L 35/00* (2016.08); *A61K 36/00* (2013.01); *A23V 2002/00* (2013.01)

(58) Field of Classification Search
None
See application file for complete search history.

(56) References Cited

FOREIGN PATENT DOCUMENTS

WO   2015/107514   7/2015

OTHER PUBLICATIONS

Bousvaros et al. NASPGHAN. "A Case-Based Monograph Focusing on Pediatric IBD" <https://www.naspghan.org/files/documents/pdfs/cme/podcasts/MonitoringDiseaseActivity_PediatricIBDPatients.pdf. 2009> (Year: 2009).*
Nestle, Modulen IBD, downloaded online Aug. 12, 2020 at <https://www.nestlehealthscience.eo.uk/brands/modulen/modulen-ibd>.
Deborah Herman, Crohn's Disease and The Dangers of Soy, published online on Jul. 21, 2012.https://deborah-herman.com/2012/07/crohns-disease-and-the-dangers-of-soy/ (Year: 2012).
Crohn's &Colitis Foundation, Facts about Inflammatory Bowel Diseases, published: May 1, 2011. (Year: 2011).
Hou et al., Perspectives in Clinical Gastroenterology and Hepatology, Diet and Inflammatory Bowel Disease: Review of Patient-Targeted Recommendations, Clinical Gastroenterology and Hepatology 2014;12:1592-1600. (Year: 2014).
Turner, Appraisal of the Pediatric Crohn's Disease Activity Index on Four Prospectively Collected Datasets: Recommended Cutoff Values and Clinimetric Properties, Am J Gastroenterol 201 O; 105:2085-2092; doi: 10.1038/ajg.2010.143; published online Apr. 6, 2010. (Year: 2010).
Best, Predicting the Crohn_s Disease Activity Index From the Harvey-Bradshaw Index, Inflamm Bowel Dis & vol. 12, No. 4, Apr. 2006. (Year: 2006).
Pearson et al., Food intolerance and Crohn's disease, Gut 1993; 34: 783-787. (Year: 1993).
Johnston et al., High-Protein, Low-Fat Diets Are Effective for Weight Loss and Favorably Alter Biomarkers in Healthy Adults, J. Nutr . 134: 586-591,2004 (Year: 2004).
International Search Report for PCT/IL2015/050028, dated Apr. 26, 2015.
Written Opinion of the International Search Authority for PCT/IL2015/050028, dated Apr. 26, 2015.
Intenational Preliminary Report on Patentability Chapter I for PCT/IL2015/050028, dated Jul. 19, 2016.
Triggs Ch. M. et al., "Dietary factors in chronic inflammation: Food tolerances and intolerances of a New Zealand Caucasian Crohn's disease population", Mutation Research/Fundamental and Molecular Mechanisms of Mutagenesis, vol. 690, Issues 1-2, Aug. 7, 2010, pp. 123-138, Abstract only.
Steinhart A.H. et al., "Crohn's & Colitis Diet Guide: Includes 150 Recipes", Apr. 11, 2008, Retrieved from: http://www.dietsinreview.com/diets/crohns-disease-diet/.

* cited by examiner

*Primary Examiner* — Nicole P Babson
(74) *Attorney, Agent, or Firm* — K&L Gates LLP

(57) ABSTRACT

The invention relates to a composition and method for induction of remission of Crohn's disease. More specifically, the composition offers an exclusion diet that reduces exposure to dietary components shown to induce inflammation in Crohn's disease patients.

8 Claims, 3 Drawing Sheets

COMPOSITION AND METHOD EFFECTIVE FOR INDUCTION OF REMISSION OF CROHN'S DISEASE

CROSS REFERENCE TO RELATED APPLICATIONS

This application is a continuation of U.S. application Ser. No. 15/307,008 filed Oct. 27, 2016, which is a National Stage of International Application No. PCT/IL2015/050028 filed Jan. 7, 2015, which claims priority to Provisional Patent Application No. 61/928,024 filed Jan. 16, 2014, the entire contents of which are incorporated herein by reference.

FIELD OF THE INVENTION

The invention relates to a composition and method for induction of remission of Crohn's disease. More specifically, the composition offers an exclusion diet that reduces exposure to dietary components shown to induce inflammation in Crohn's disease patients.

BACKGROUND

Crohn's disease (CD) is caused by a combination of environmental and genetic factors, and a major role of the microbiota has been postulated in the pathogenesis of the disease. (1) Although progress has been achieved in determining the genetic and immune basis for susceptibility to the disease, understanding the contribution of potential environmental risk factors has been difficult. (2-5) All current therapies are aimed at the downstream events, namely intervention directed towards the host inflammatory response. An alternative environmental factor, which has not been adequately explored in human subjects, is the effect of diet on CD. Diet has an effect on the composition of the intestinal microbiome and gut immune status. (5-7) We have previously proposed that CD may arise from a sequence of events involving changes in the microbiome, intestinal permeability leading to bacterial adherence or penetration of the epithelium, and subsequent stimulation of the adaptive immune response leading to tissue damage. 8-11 We have termed this sequence the Bacterial Penetration Cycle Hypothesis. 12 The most important evidence-linking diet to CD comes from dietary interventions in children with active CD. (12-16) Exclusive enteral nutrition (EEN) is a well-documented method of treatment. It involves placing children on a strict diet composed only of a single polymeric formula, as the sole source of nutrition over 6 to 8 weeks. Use of this treatment method, early in the disease, results in clinical remission in 50% to 80% of children by week 8 with no additional pharmacological treatment. 12-16 Previous studies and clinical experience have shown that partial enteral nutrition (PEN) with 50% of calories from a formula with free diet is ineffective in inducing complete remission or reducing acute phase reactants, suggesting that the effect of EEN appears to depend, at least in part, on exclusion of free diet. (17) In addition, since the mechanism of response or the triggering foods are unknown, there is no evidence based follow on strategy, to prevent recurrence upon re-exposure to normal diet. Therefore it is crucial to try to evaluate which of the excluded dietary components in EEN are responsible for the effect, to allow transition to a safe whole food diet. We report a dietary intervention that involves whole foods but reduces exposure to dietary components have been shown to induce inflammation, change the microbiome, affect the mucous layer, increase IP or adherence and translocation of bacteria in rodent or cell line models. (18-24) Our experience started with 2 adolescents who had difficulty in continuing EEN despite an initial clinical response, they were placed on this structured diet with only 50% of calories from Modulen (Nestle, Switzerland), and went into complete remission with normalization of acute phase reactants. The diet subsequently became the standard of practice for patients with luminal uncomplicated mild-to-moderate disease who were not willing to use EEN. We report our experience with use of 50% PEN with CDED or CDED alone as the primary method for induction of remission in children and young adults with mild-to moderate active CD.

SUMMARY

The present invention provides a method for providing a diet for a Crohn's disease patient, the method comprising two stages: stage 1 which is provided in weeks 1-6 and stage 2 which is provided in weeks 7-12; wherein stage 1 comprises the step of consuming the following food products per day: at least one portion of fresh chicken breast or fresh fish, two eggs, two peeled potatoes and two bananas; unlimited amounts of products selected from a group consisting of: white rice, rice noodles without preservatives, olive oil, canola oil, salt, pepper, paprika, cinnamon stick, fresh herb leaves, fresh onion, fresh garlic, fresh ginger, fresh lemon, water, soda, herbal teas prepared from fresh leaves; no more than the following: 3 tablespoons of honey, 3 teaspoons of sugar; 2 tomatoes, 2 peeled cucumbers, 1 cup fresh spinach, 1 avocado, 5 Strawberries, 1 slice melon, one glass of freshly squeezed orange juice; further wherein stage 2 comprises the step of consuming the following food products per day:

at least one portion of fresh chicken breast or fresh fish, two eggs, two peeled potatoes and two bananas; unlimited amounts of products selected from a group consisting of: white rice, rice noodles without preservatives, olive oil, canola oil, salt, pepper, paprika, cinnamon stick, fresh herb leaves, fresh onion, fresh garlic, fresh ginger, fresh lemon, water, soda, herbal teas prepared from fresh leaves, quinoa; no more than the following: 3 tablespoons of honey, 3 teaspoons of sugar; 2 tomatoes, 2 peeled cucumbers, 1 cup fresh spinach, 1 avocado, 5 Strawberries, 1 Slice Melon, one cup of fresh lettuce, ½ red bell pepper, 4 fresh mushrooms, 1 zucchini, 2 small pieces of broccoli, 6 whole almonds or 6 walnut halves, a ½ cup of dried chickpeas or lentils; hereby providing dietary components comprising food with reduced content of animal fat, dairy product, gluten, taurine, yeast sulfites and emulsifiers.

It is another object of the current invention to disclose the method as defined in any of the above, wherein the diet is provided in combination with enteral nutrition.

It is another object of the current invention to disclose the method as defined in any of the above, wherein the enteral nutrition provides about 50% of daily caloric intake consumed in the stage 1.

It is another object of the current invention to disclose the method as defined in any of the above, wherein the enteral nutrition provides about 25% of the daily caloric intake consumed in the stage 1.

It is another object of the current invention to disclose the method as defined in any of the above, wherein the patient is selected from a group consisting of: adult, young adult, children, and any combination thereof.

It is another object of the current invention to disclose the method as defined in any of the above, wherein the patient is suffering from mild to moderate Crohn's disease.

It is another object of the current invention to disclose the method as defined in any of the above, wherein the fresh herb leaves are selected from a group consisting of mint leaves, oregano, rosemary, sage, basil, thyme, parsley, dill, and any combination thereof.

It is another object of the current invention to disclose the method as defined in any of the above, wherein the food products in the stage 1 and the stage 2 additionally comprise additional products if the patient has no strictures; the additional products comprise products selected from a group consisting of: no more than 1 peeled apple, no more than 1 carrot.

It is another object of the current invention to disclose the method as defined in any of the above, wherein the no more than 1 peeled apple can be replaced in stage 2 with a fruit selected from a group consisting of no more than 1 pear, no more than one nectarine, no more than one kiwi, no more than one peach, and any combination thereof.

It is another object of the current invention to disclose the method as defined in any of the above, wherein the food products in the stage 1 additionally comprise no more than 200 g of unprocessed beef lean steak per week from week 4 and onwards.

It is another object of the current invention to disclose the method as defined in any of the above, wherein the food products in the stage 2 additionally comprise no more than 200 g of unprocessed beef lean steak per week.

It is another object of the current invention to disclose the method as defined in any of the above, wherein the food products in the stage 2 additionally comprise no more than 200 g of unprocessed beef lean steak per.

It is another object of the current invention to disclose the method as defined in any of the above, wherein the food products in the stage 2 additionally comprise no more 1 slice of whole grain bread from week 8 and onwards.

It is another object of the current invention to disclose the method as defined in any of the above, wherein the vegetables in the food products of stage 2 may be gradually replaced with other vegetables from week 8 and onwards; the other vegetables are selected from a group consisting of: beets, squash, cabbage, cauliflower, and any combination thereof.

It is another object of the current invention to disclose the method as defined in any of the above, wherein the food products of stage 2 additionally comprise no more than a small can of tuna packed in oil up to twice a week.

It is another object of the current invention to disclose the method as defined in any of the above, wherein the almonds or walnuts are unsalted and unprocessed.

It is another object of the current invention to disclose the method as defined in any of the above, wherein the food products of the stage 1 and the stage 2 are fresh.

It is another object of the current invention to disclose the method as defined in any of the above, wherein the avocado is to be consumed over at least two meals.

It is another object of the current invention to disclose the method as defined in any of the above, wherein the 2 peeled potatoes are to be consumed over at least two meals.

It is another object of the current invention to disclose the method as defined in any of the above, wherein the food products may be processed in a manner selected from a group consisting of grilling, frying, baking, boiling, broiling, and any combination thereof.

It is another object of the current invention to disclose the method as defined in any of the above, wherein after 6 weeks of practicing the method the PCDAI without the height item was less than 7.5 for the patients which are children and young adults and the HBI index was less than 3 for the patients which are adults.

It is another object of the current invention to disclose the method as defined in any of the above, wherein after 12 weeks of practicing the method the PCDAI drop at least about 12.5 points for children and young adults and a drop in HBI of at least 2 points.

It is another object of the current invention to disclose the method as defined in any of the above, wherein the stage 1 and the stage 2 additionally comprise the step of not consuming the following foods: dairy products of any kind, margarine, wheat, breakfast cereals, breads and baked goods of any kind, yeast for baking, granola, power bars or granola bars, gluten free products not listed above, soy products, potato or corn flour, corn, frozen vegetables, frozen fruits, processed or smoked meats and fish, sauces, salad dressings, syrups and jams of any kind, tomato paste, canned products, dried fruits, packaged snacks, soft drinks, fruit juices and sweetened beverages, vitamin waters, alcoholic beverages, coffee, frozen drinks, candy, chocolate, cake, cookies, chewing gum, artificial sweeteners, vinegar, mixed spices, curry, nuts.

The present invention further provides a range of food products for a Crohn's disease remission diet; the range of food products comprise a first range of food products and a second range of food products; the first range of food products is adapted to be consumed in weeks 1-6 of the diet and the second range of food products is adapted to be consumed in weeks 7-12; wherein the first range of food products comprise the following food products per day: at least one portion of fresh chicken breast or fresh fish, two eggs, two peeled potatoes and two bananas; unlimited amounts of products selected from a group consisting of: white rice, rice noodles without preservatives, olive oil, canola oil, salt, pepper, paprika, cinnamon stick, fresh herb leaves, fresh onion, fresh garlic, fresh ginger, fresh lemon, water, soda, herbal teas prepared from fresh leaves, lentils, dry chickpeas; no more than the following: 3 tablespoons of honey, 3 teaspoons of sugar; 2 tomatoes, 2 peeled cucumbers, 1 cup fresh spinach, 1 avocado, 5 Strawberries, 1 slice melon, one glass of freshly squeezed orange juice; further wherein the second range of food products comprise the following food products per day: at least one portion of fresh chicken breast or fresh fish, two eggs, two peeled potatoes and two bananas; unlimited amounts of products selected from a group consisting of: white rice, rice noodles without preservatives, olive oil, canola oil, salt, pepper, paprika, cinnamon stick, fresh herb leaves, fresh onion, fresh garlic, fresh ginger, fresh lemon, water, soda, herbal teas prepared from fresh leaves, quinoa; no more than the following: 3 tablespoons of honey, 3 teaspoons of sugar; 2 tomatoes, 2 peeled cucumbers, 1 cup fresh spinach, 1 avocado, 5 Strawberries, 1 Slice Melon, one cup of fresh lettuce, ½ red bell pepper, 4 fresh mushrooms, 1 zucchini, 2 small pieces of broccoli, 6 whole almonds or 6 walnut halves; thereby providing dietary components comprising food with reduced content of animal fat, dairy product, gluten and emulsifiers.

It is another object of the current invention to disclose the range of foods as defined in any of the above, wherein the diet is provided in combination with enteral nutrition.

It is another object of the current invention to disclose the range of foods as defined in any of the above, wherein the enteral nutrition provides about 50% of daily caloric intake consumed with the first range of foods.

It is another object of the current invention to disclose the range of foods as defined in any of the above, wherein the enteral nutrition provides about 25% of the daily caloric intake with the second range of foods.

It is another object of the current invention to disclose the range of foods as defined in any of the above, wherein the range of food is adapted to be provided to a patient selected from a group consisting of: adult, young adult, children, and any combination thereof.

It is another object of the current invention to disclose the range of foods as defined in any of the above, wherein the range of food is adapted to be provided to a patient suffering from mild to moderate Crohn's disease.

It is another object of the current invention to disclose the range of foods as defined in any of the above, wherein the fresh herb leaves are selected from a group consisting of mint leaves, oregano, rosemary, sage, basil, thyme, parsley, dill, and any combination thereof.

It is another object of the current invention to disclose the range of foods as defined in any of the above, wherein the first range of food products and the second range of food products additionally comprise additional products if the patient has no strictures; the additional products comprise products selected from a group consisting of: no more than 1 peeled apple, no more than 1 carrot.

It is another object of the current invention to disclose the range of foods as defined in any of the above, wherein the no more than 1 peeled apple can be replaced in the second range of food products with a fruit selected from a group consisting of no more than 1 pear, no more than one nectarine, no more than one kiwi, no more than one peach, and any combination thereof.

It is another object of the current invention to disclose the range of foods as defined in any of the above, wherein the first range of food products additionally comprise no more than 200 g of unprocessed beef lean steak per week from week 4 and onwards.

It is another object of the current invention to disclose the range of foods as defined in any of the above, wherein the second range of food products additionally comprise no more than 200 g of unprocessed beef lean steak.

It is another object of the current invention to disclose the range of foods as defined in any of the above, wherein the food products in the second range of food products additionally comprise no more than 200 g of unprocessed beef lean steak per.

It is another object of the current invention to disclose the range of foods as defined in any of the above, wherein the second range of food products additionally comprise no more 1 slice of whole grain bread from week 8 and onwards.

It is another object of the current invention to disclose the range of foods as defined in any of the above, wherein the vegetables in the second range of food products may be gradually replaced with other vegetables from week 8 and onwards; the other vegetables are selected from a group consisting of: beets, squash, cabbage, cauliflower, and any combination thereof.

It is another object of the current invention to disclose the range of foods as defined in any of the above, wherein the second range of food products additionally comprise no more than a small can of tuna up to twice a week.

It is another object of the current invention to disclose the range of foods as defined in any of the above, wherein the almonds or walnuts are unsalted and unprocessed.

It is another object of the current invention to disclose the range of foods as defined in any of the above, wherein the first range of food products and the second range of food products are fresh.

It is another object of the current invention to disclose the range of foods as defined in any of the above, wherein the avocado is to be consumed over at least two meals.

It is another object of the current invention to disclose the range of foods as defined in any of the above, wherein the 2 peeled potatoes are to be consumed over at least two meals.

It is another object of the current invention to disclose the range of foods as defined in any of the above, wherein the food products may be processed in a manner selected from a group consisting of grilling, frying, baking, boiling, broiling, and any combination thereof.

It is another object of the current invention to disclose the range of foods as defined in any of the above, wherein after 6 weeks of practicing the diet the PCDAI without the height item was less than 7.5 for the patients which are children and young adults and the HBI index was less than 3 for the patients which are adults.

It is another object of the current invention to disclose the range of foods as defined in any of the above, wherein after 12 weeks of practicing the diet the PCDAI drop at least about 12.5 points for children and young adults and a drop in HBI of at least 2 points.

It is another object of the current invention to disclose the range of foods as defined in any of the above, wherein the first range of food products and the second range of food products does not include the following foods: The method of claim 1, wherein the stage 1 and the stage 2 additionally comprise the step of not consuming the following foods: dairy products of any kind, margarine, wheat, breakfast cereals, breads and baked goods of any kind, yeast for baking, granola, power bars or granola bars, gluten free products not listed above, soy products, potato or corn flour, corn, frozen vegetables, frozen fruits, processed or smoked meats and fish, sauces, salad dressings, syrups and jams of any kind, tomato paste, canned products, dried fruits, packaged snacks, soft drinks, fruit juices and sweetened beverages, vitamin waters, alcoholic beverages, coffee, frozen drinks, candy, chocolate, cake, cookies, chewing gum, artificial sweeteners, vinegar, mixed spices, curry, nuts.

The present invention further provides a method of preventing Crohn's disease to be followed for at least 12 weeks, the method comprising the following steps of limiting all food intake to a first range of food products in weeks 1-6 and a second range of food products in weeks 7-12; wherein the first range of food products comprise the following food products per day: at least one portion of fresh chicken breast or fresh fish, two eggs, two peeled potatoes and two bananas; unlimited amounts of products selected from a group consisting of: white rice, olive oil, canola oil, salt, pepper, paprika, cinnamon stick, fresh herb leaves, fresh onion, fresh garlic, fresh ginger, fresh lemon, water, soda, herbal teas prepared from fresh leaves, lentils, dry chickpeas; no more than the following: one portion of rice noodles without preservatives, 3 tablespoons of honey, 3 teaspoons of sugar; 2 tomatoes, 2 peeled cucumbers, 1 cup fresh spinach, 1 avocado, 5 Strawberries, 1 slice melon, one glass of freshly squeezed orange juice; further wherein the second range of food products comprise the following food products per day: at least one portion of fresh chicken breast or fresh fish, two eggs, two peeled potatoes and two bananas; unlimited amounts of products selected from a group consisting of: white rice, olive oil, canola oil, salt, pepper, paprika, cinnamon stick, fresh herb leaves, fresh onion, fresh garlic, fresh ginger, fresh lemon, water, soda, herbal teas prepared from fresh leaves, quinoa; no more than the following: one portion of rice noodles without preservatives, 3 tablespoons of honey, 3 teaspoons of sugar; 2 tomatoes, 2 peeled cucumbers, 1 cup fresh spinach, 1 avocado, 5 Strawberries, 1 Slice Melon, one cup of fresh lettuce, ½ red bell pepper, 4 fresh mushrooms, 1 zucchini, 2 small pieces of broccoli, 6 whole almonds or 6 walnut halves; thereby providing dietary components comprising food with reduced content of animal fat, dairy product, gluten and emulsifiers.

It is another object of the current invention to disclose the method as defined in any of the above, wherein the food intake is provided in combination with enteral nutrition.

It is another object of the current invention to disclose the method as defined in any of the above, wherein the enteral nutrition provides about 50% of daily caloric intake when consumed with the first range of foods.

It is another object of the current invention to disclose the method as defined in any of the above, wherein the enteral nutrition provides about 25% of the daily caloric intake when consumed with the second range of foods.

It is another object of the current invention to disclose the method as defined in any of the above, wherein the limiting of food intake is carried out by a patient selected from a group consisting of: adult, young adult, children, and any combination thereof.

It is another object of the current invention to disclose the method as defined in any of the above, wherein the limiting of food intake is carried out by a patient suffering from mild to moderate Crohn's disease.

It is another object of the current invention to disclose the method as defined in any of the above, wherein the fresh herb leaves are selected from a group consisting of mint leaves, oregano, rosemary, sage, basil, thyme, parsley, dill, and any combination thereof.

It is another object of the current invention to disclose the method as defined in any of the above, wherein the first range of food products and the second range of food products additionally comprise additional products if the patient has no strictures; the additional products comprise products selected from a group consisting of: no more than 1 peeled apple, no more than 1 carrot.

It is another object of the current invention to disclose the method as defined in any of the above, wherein the no more than 1 peeled apple can be replaced in the second range of food products with a fruit selected from a group consisting of no more than 1 pear, no more than one nectarine, no more than one kiwi, no more than one peach, and any combination thereof.

It is another object of the current invention to disclose the method as defined in any of the above, wherein the first range of food products additionally comprise no more than 200 g of unprocessed beef lean steak per week from week 4 and onwards.

It is another object of the current invention to disclose the method as defined in any of the above, wherein the second range of food products additionally comprise no more than 200 g of unprocessed beef lean steak.

It is another object of the current invention to disclose the method as defined in any of the above, wherein the second range of food products additionally comprise no more 1 slice of whole grain bread from week 8 and onwards.

It is another object of the current invention to disclose the method as defined in any of the above, wherein the vegetables in the second range of food products may be gradually replaced with other vegetables from week 8 and onwards; the other vegetables are selected from a group consisting of: beets, squash, cabbage, cauliflower, and any combination thereof.

It is another object of the current invention to disclose the method as defined in any of the above, wherein the second range of food products additionally comprise no more than a small can of tuna up to twice a week.

It is another object of the current invention to disclose the method as defined in any of the above, wherein the almonds or walnuts are unsalted and unprocessed.

It is another object of the current invention to disclose the method as defined in any of the above, wherein the first range of food products and the second range of food products are fresh.

It is another object of the current invention to disclose the method as defined in any of the above, wherein the avocado is to be consumed over at least two meals.

It is another object of the current invention to disclose the method as defined in any of the above, wherein the 2 peeled potatoes are to be consumed over at least two meals.

It is another object of the current invention to disclose the method as defined in any of the above, wherein the food products may be processed in a manner selected from a group consisting of grilling, frying, baking, boiling, broiling, and any combination thereof.

It is another object of the current invention to disclose the method as defined in any of the above, wherein after 6 weeks of practicing the diet the PCDAI without the height item was less than 7.5 for the patients which are children and young adults and the HBI index was less than 3 for the patients which are adults.

It is another object of the current invention to disclose the method as defined in any of the above, wherein after 12 weeks of practicing the diet the PCDAI drop at least about 12.5 points for children and young adults and a drop in HBI of at least 2 points.

It is another object of the current invention to disclose the method as defined in any of the above, wherein the first range of food products and the second range of food products does not include the following foods: The method of claim 1, wherein the stage 1 and the stage 2 additionally comprise the step of not consuming the following foods: dairy products of any kind, margarine, wheat, breakfast cereals, breads and baked goods of any kind, yeast for baking, granola, power bars or granola bars, gluten free products not listed above, soy products, potato or corn flour, corn, frozen vegetables, frozen fruits, processed or smoked meats and fish, sauces, salad dressings, syrups and jams of any kind, tomato paste, canned products, dried fruits, packaged snacks, soft drinks, fruit juices and sweetened beverages, vitamin waters, alcoholic beverages, coffee, frozen drinks, candy, chocolate, cake, cookies, chewing gum, artificial sweeteners, vinegar, mixed spices, curry, nuts.

The present invention further provides a daily prepackaged therapeutic meal of a daily diet for consumption to be consumed daily for at least 12 weeks by a Crohn's disease patient; the meal prepackaged therapeutic meal comprising food products for daily consumption; the food products comprising a first range of food products in the prepackaged therapeutic meal adapted to be consumed in weeks 1-6 and a second range of food products in the prepackaged therapeutic meal adapted to be consumed in weeks 7 and onwards; wherein the first range of food products comprise the following food products per day: at least one portion of fresh chicken breast or fresh fish, two eggs, two peeled potatoes and two bananas; unlimited amounts of products selected from a group consisting of: white rice, rice noodles without preservatives, olive oil, canola oil, salt, pepper, paprika, cinnamon stick, fresh herb leaves, fresh onion, fresh garlic, fresh ginger, fresh lemon, water, soda, herbal teas prepared from fresh leaves, lentils, dry chickpeas; no more than the following: 3 tablespoons of honey, 3 teaspoons of sugar; 2 tomatoes, 2 peeled cucumbers, 1 cup fresh spinach, 1 avocado, 5 Strawberries, 1 slice melon, one glass of freshly squeezed orange juice; further wherein the second range of food products comprise the following food products per day: at least one portion of fresh chicken breast or fresh fish, two eggs, two peeled potatoes and two bananas; unlimited amounts of products selected from a group consisting of: white rice, rice noodles without preservatives, olive oil, canola oil, salt, pepper, paprika, cinnamon stick, fresh herb leaves, fresh onion, fresh garlic, fresh ginger, fresh lemon, water, soda, herbal teas prepared from fresh leaves, quinoa; no more than the following: 3 tablespoons of honey, 3 teaspoons of sugar; 2 tomatoes, 2 peeled cucumbers, 1 cup fresh spinach, 1 avocado, 5 Strawberries, 1 Slice Melon, one cup of fresh lettuce, ½ red bell pepper, 4 fresh mushrooms, 1 zucchini, 2 small pieces of broccoli, 6 whole almonds or 6 walnut halves; thereby providing daily dietary components comprising food with reduced content of animal fat, dairy product, gluten and emulsifiers.

It is another object of the current invention to disclose the daily prepackaged therapeutic meal as defined in any of the above, wherein the prepackaged therapeutic meal is provided in combination with enteral nutrition.

It is another object of the current invention to disclose the daily prepackaged therapeutic meal as defined in any of the above, wherein the enteral nutrition provides about 50% of daily caloric intake in the prepackaged therapeutic meal adapted to be consumed in weeks 1-6.

It is another object of the current invention to disclose the daily prepackaged therapeutic meal as defined in any of the above, wherein the enteral nutrition provides about 25% of the daily caloric intake in the prepackaged therapeutic meal adapted to be consumed in weeks 7 and onwards.

It is another object of the current invention to disclose the daily prepackaged therapeutic meal as defined in any of the above, wherein the daily prepackaged therapeutic meal is adapted to be provided to a patient selected from a group consisting of: adult, young adult, children, and any combination thereof.

It is another object of the current invention to disclose the daily prepackaged therapeutic meal as defined in any of the above, wherein the daily prepackaged therapeutic meal is adapted to be provided to a patient suffering from mild to moderate Crohn's disease.

It is another object of the current invention to disclose the daily prepackaged therapeutic meal as defined in any of the above, wherein the fresh herb leaves are selected from a group consisting of mint leaves, oregano, rosemary, sage, basil, thyme, parsley, dill, and any combination thereof.

It is another object of the current invention to disclose the daily prepackaged therapeutic meal as defined in any of the above, wherein the first range of food products and the second range of food products additionally comprise additional products if the patient has no strictures; the additional products comprise products selected from a group consisting of: no more than 1 peeled apple, no more than 1 carrot.

It is another object of the current invention to disclose the daily prepackaged therapeutic meal as defined in any of the above, wherein the no more than 1 peeled apple can be replaced in the second range of food products with a fruit selected from a group consisting of no more than 1 pear, no more than one nectarine, no more than one kiwi, no more than one peach or one pear, and any combination thereof.

It is another object of the current invention to disclose the daily prepackaged therapeutic meal as defined in any of the above, wherein the first range of food products additionally comprise no more than 200 g of unprocessed beef lean steak per week from week 4 and onwards.

It is another object of the current invention to disclose the daily prepackaged therapeutic meal as defined in any of the above, wherein the second range of food products additionally comprise no more than 200 g of unprocessed beef lean steak.

It is another object of the current invention to disclose the daily prepackaged therapeutic meal as defined in any of the above, wherein the second range of food products additionally comprise no more 1 slice of whole grain bread from week 8 and onwards.

It is another object of the current invention to disclose the daily prepackaged therapeutic meal as defined in any of the above, wherein the vegetables in the second range of food products may be gradually replaced with other vegetables from week 8 and onwards; the other vegetables are selected from a group consisting of: beets, squash, cabbage, cauliflower, and any combination thereof.

It is another object of the current invention to disclose the daily prepackaged therapeutic meal as defined in any of the above, wherein the second range of food products additionally comprise no more than a small can of tuna up to twice a week.

It is another object of the current invention to disclose the daily prepackaged therapeutic meal as defined in any of the above, wherein the almonds or walnuts are unsalted and unprocessed.

It is another object of the current invention to disclose the daily prepackaged therapeutic meal as defined in any of the above, wherein the first range of food products and the second range of food products are fresh.

It is another object of the current invention to disclose the daily prepackaged therapeutic meal as defined in any of the above, wherein the avocado is to be consumed over at least two meals.

It is another object of the current invention to disclose the daily prepackaged therapeutic meal as defined in any of the above, wherein the 2 peeled potatoes are to be consumed over at least two meals.

It is another object of the current invention to disclose the daily prepackaged therapeutic meal as defined in any of the above, wherein the food products may be processed in a manner selected from a group consisting of grilling, frying, baking, boiling, broiling, and any combination thereof.

It is another object of the current invention to disclose the daily prepackaged therapeutic meal as defined in any of the above, wherein after 6 weeks of consuming the daily prepackaged therapeutic meal the PCDAI without the height item was less than 7.5 for the patients which are children and young adults and the HBI index was less than 3 for the patients which are adults.

It is another object of the current invention to disclose the daily prepackaged therapeutic meal as defined in any of the above, wherein after 12 weeks of consuming the daily prepackaged therapeutic meal the PCDAI drop at least about 12.5 points for children and young adults and a drop in HBI of at least 2 points.

It is another object of the current invention to disclose the daily prepackaged therapeutic meal as defined in any of the above, wherein the first range of food products and the second range of food products does not include the following foods: The method of claim 1, wherein the stage 1 and the stage 2 additionally comprise the step of not consuming the following foods: dairy products of any kind, margarine, wheat, breakfast cereals, breads and baked goods of any kind, yeast for baking, granola, power bars or granola bars, gluten free products not listed above, soy products, potato or corn flour, corn, frozen vegetables, frozen fruits, processed or smoked meats and fish, sauces, salad dressings, syrups and jams of any kind, tomato paste, canned products, dried fruits, packaged snacks, soft drinks, fruit juices and sweetened beverages, vitamin waters, alcoholic beverages, coffee, frozen drinks, candy, chocolate, cake, cookies, chewing gum, artificial sweeteners, vinegar, mixed spices, curry, nuts.

BRIEF DESCRIPTION OF THE FIGURES

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

In the accompanying drawings.

DETAILED DESCRIPTION OF THE INVENTION

Figure 1A:
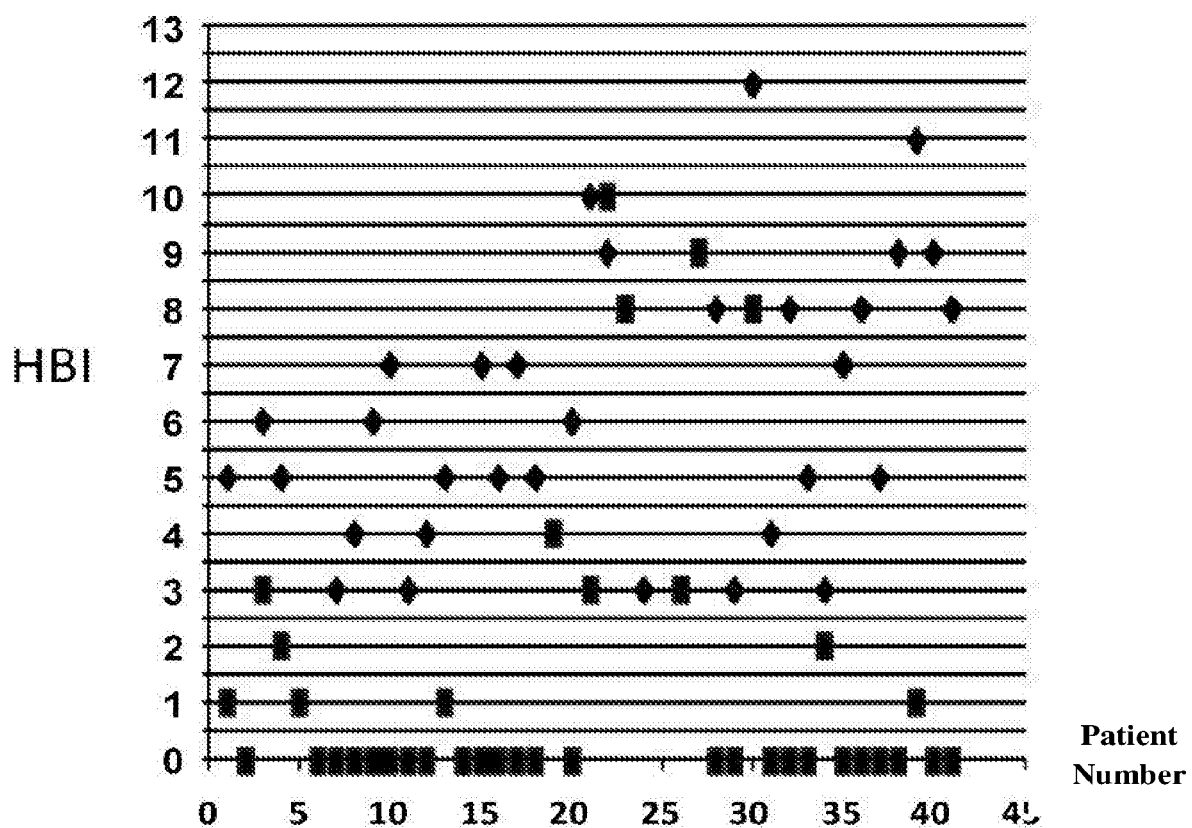
FIG. 1A shows changes in 45 patients in HBI from the beginning of the diet and after 6 weeks of preforming the diet.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

The essence of the present invention is to provide a method and a composition of a diet for a Crohn's disease patient. More specifically the method comprise administering food products which reduces exposure to dietary components shown to induce inflammation, mainly food with reduced content of animal fat, dairy product, gluten and emulsifiers.

Animal fat is problematic because high exposure in animal models causes dysbiosis, reduces mucous expression, allows colonization with adherent invasive E. coli and increases intestinal permeability (19). Sulphide reducing bacteria can cause intestinal inflammation and dysbiosis. Thus taurine conjugated bile acids and taurine exposure should be limited (21). Beef protein is problematic since it is high in Taurine and contains Heme, both which might aggravate colitis (Le Leu R K et al. Dig Dis Sci (2013) 58:3475-3482). Processed meats may contain nitrites, sulphites, sulfated products and emulsifiers which are prohibited. Sulphites and sulphate are prohibited since they can be a substrate for sulfide reducing bacteria. Taurine intake should be less than 100 mg day High fat high sugar diets may cause dysbiosis, reduces mucous expression, allow colonization with adherent invasive E. coli and increase intestinal permeability (19). On the other hand, certain starch containing carbohydrates are beneficial since they contain resistant starches which can be turned into short chain fatty acids. Potato and rice products are good sources and relatively available starches. Excess carbohydrates from other sources would increase the load of fiber beyond 18-25 grams day which is ideal for the diet.

Fibers are positive but limited to 18-25 grams day. In order to supply enough calories with beneficial oils Avocado appears on the list of allowed food. Bananas (plantain family) are obligatory in the diet since they are a good source of soluble fiber and resistant starch as well as the plantain fiber may retard translocation of adherent invasive E coli.

Disallowed foods listed below cause dysbiosis, impair intestinal permeability, affect the mucous layer, enhance biofilms, bacterial adherence and translocation. The list of products that may cause one of these effects includes animal fat, polysorbate 80, carboxymethycellulose, carageenans, sulfites, maltodextrin, sucralose or aspartame, gluten, yeasts and sulphites.

Processed food is prohibited since manufacturers add sulfites to processed foods as a preservative and to improve its appearance. All cheeses contain some sulfites, which develop during the aging process. Maraschino cherries, pickled onions, wine vinegar, pickles, olives and condiments such as horseradish might also contain sulfites. Jams, jellies, foods containing gelatin, maple syrup, corn syrup and dried-soup mixes can contain sulfites. Check grains such as pizza, quiche or pie crust, flour tortillas, spinach pasta, filled crackers or noodle/rice mixes for sulfites. Sulfites are added to shellfish to maintain the color of their shells. Canned seafood and seafood soups and dried cod can also contain added sulfites. Sulfites prevent melanosis, or black spot on shrimp and lobster. Processors cannot add sulfites to red meat because they add color that can make the meat appear fresher than it actually is. Processed foods that contain meat, such as beef stew, might have sulfites added. The United States Food and Drug Administration prohibits the addition of sulfites to fresh fruits and vegetables, except for potato dishes. After processing plants peel potatoes, freezing them at temperatures of less than 45 degrees Fahrenheit causes them to turn brown rapidly when the starches in the potatoes convert to sugars. The processing plants add sulfites to prevent browning. Dried fruits often contain added sulfites, including dried apricots, dried fruit snacks and golden grapes. Some dried fruits can contain sulfite amounts as high as 2,000 parts per million, according to the University of Nebraska-Lincoln.

Sulphites which may provide a substrate for sulfide reducing bacteria just like taurine, are added to prevent spotting mould in processed meats, processed doughs, dried fruits and fruit preserves, shellfish, frozen vegetables such as potatoes fruit juices and certain alcoholic beverages, most notably wines and beer.

The term "Crohn's disease (CD)" refers hereinafter to a type of inflammatory bowel disease that may affect any part of the gastrointestinal tract from mouth to anus. Symptoms often include: abdominal pain, diarrhea (which may be bloody if inflammation is severe), fever and weight loss. Other complications may occur outside the gastrointestinal tract and include: anemia, skin rashes, arthritis, inflammation of the eye, and tiredness. Bowel obstruction also commonly occurs and those with the disease are at greater risk of bowel cancer.

The term "portion" refers hereinafter to normal serving size of a child, young adult or and an adult. More specifically the term relates to the amount of 150-300 grams.

The term "about" refers hereinafter to ±25% of the defined amount or measure or value.

The term "enteral nutrition" refers hereinafter to palatable polymeric formulas containing about 1 Kcal/ml. For example Modulen™ (Nestle, Switzerland) or Pediasure (Abbott, USA). The use of enteral nutrition guarantees a minimum intake of calcium and protein, and ensure growth, which is a significant problem in children with active Crohn's disease.

The term "daily caloric intake" refers hereinafter to the daily calorie intake that is considered to be sufficient to meet the requirements of 97-98% of healthy individuals. The caloric intake for adults are 2,700 and 2,100 kcal for men and women, respectively. The caloric intake needed by children range from 900/day for a 1-year-old to 1,800 for a 14-18-year-old girl and 2500 for a 14-18-year-old boy.

The term "children" refers hereinafter to a human being at the age range of 6-12.

The term "young adult" refers hereinafter to a human being at the age range of 12-17.

The term "adult" refers herein after to a human being aged 18 or more.

The term "Crohn's disease activity index (CDAI)" refers hereinafter to a research tool used to quantify the symptoms of patients with Crohn's disease. This tool is used in studies done on medications used to treat Crohn's disease in order to define response or remission of the disease.

Remission of Crohn's disease is defined as CDAI below 150. Severe disease was defined as a value of greater than 450. Research studies on medications in Crohn's disease define response as a fall of the CDAI of greater than 70 points.

The index consists of eight factors, each summed after adjustment with a weighting factor. The components of the CDAI and weighting factors are the following:

| Clinical or laboratory variable | Weighting factor |
| --- | --- |
| Number of liquid or soft stools each day for seven days | x 2 |
| Abdominal pain (graded from 0-3 on severity) each day for seven days | x 5 |
| General well being, subjectively assessed from 0 (well) to 4 (terrible) each day for seven days | x 7 |
| Presence of complications(*) | x 20 |
| Taking Lomotil or opiates for diarrhea | x 30 |
| Presence of an abdominal mass (0 as none, 2 as questionable, 5 as definite) | x 10 |
| Hematocrit of <0.47 in men and <0.42 in women | x 6 |
| Percentage deviation from standard weight | x 1 |

(*)One point each is added for each set of complications: the presence of joint pains (arthralgia) or frank arthritis, inflammation of the iris or uveitis, presence of erythema nodosum, pyoderma gangrenosum, or aphthous ulcers, anal fissures, fistulae or abscesses, other fistulae, fever during the previous week.

The term "pediatric Crohn's disease activity index (PCDAI)" refers hereinafter to a multi-item measure that, in contrast to the adult-derived CDAI, includes linear growth and places less emphasis on subjectively reported symptoms but more on laboratory parameters of intestinal inflammation. The PCDAI score ranges from 0 to 100 where scores <10 reflects inactive disease, 10-30 mild disease and scores >30 moderate to severe disease. The clinically meaningful decrease to define response 15 points.

The term "Harvey Bradshaw index (HBI)" refers hereinafter to a simpler version of the CDAI for data collection purposes. It consists of only clinical parameters:
General well-being (0=very well, 1=slightly below average, 2=poor, 3=very poor, 4=terrible)
Abdominal pain (0=none, 1=mild, 2=moderate, 3=severe)
Number of liquid stools per day
Abdominal mass (0=none, 1=dubious, 2=definite, 3=tender)
Complications, as above, with one point for each.

A score of less than 5 is generally considered to represent clinical remission. Patients with a score of 8 or higher are considered to have severe disease.

The term "stricture" and/or "stenosis" refers hereinafter to constriction of the bowel lumen, as a result of incomplete aplasia, cicatricial contraction after injury or infection, leads to a syndrome of chronic or intermittent subacute abdominal pain.

The term "fresh food" refers hereinafter to any food that was prepared less than 12 hours in advance, or the whole fruits and vegetables that have been picked but have not been processed, altered, canned or have added sweeteners. In order for food to be considered fresh it cannot be frozen and thawed. This excludes fresh fish or chicken breast that are considered fresh even if frozen.

The term "beef lean steak" refers hereinafter to lean meat such as sirloin. The term does not include pre-prepared ground beef but does include lean steak grounded by the butcher or at home in to ground beef without additives.

The term "freshly squeezed orange juice" refers hereinafter to orange juice that was squeezed less than an hour before consumption without addition of chemicals or sweeteners. Orange juice from cartons or bottles are not considered fresh orange juice.

The term "C-reactive protein (CRP)" refers hereinafter to a protein found in the blood plasma, of which its levels rise in response to inflammation.

Example 1

This is a report of our experience with a combination of partial enteric nutrition (PEN) and (Crohn's disease exclusion diet) CD ED or CD ED alone, for active CD in outpatient children and young adults. Patients receiving the diet were seen between 2011 and August 2013 at a pediatric IBD center and a gastroenterology outpatient center. The current standard of practice in our unit or active outpatients who do not require hospitalization is to offer (exclusive enteral nutrition) EEN for induction along with thiopurines as the initial treatment for new onset mild to moderate CD with ileal or jejunal involvement. It is also offered as a secondary treatment after failure of other treatments.

Inclusion criteria included children and young adults with active CD, defined as a Pediatric Crohn's Disease Activity Index (PCDAI) ≥10 without the height component (25) in children or Harvey Bradshaw Index (HBI) >3 (26), available data for disease activity at baseline and at the 6 week follow up visit. The retrospective study was approved by the hospital's ethical committee.

Patients were excluded if the patient's charts were not available (n=4, 3 remission and 1 failure), if they had penetrating disease, active perianal disease or extra-intestinal disease, or if they received any other medication for inducing remission in addition to diet (n=2). Patients with strictures and evidence for active inflammation were not excluded. Patients who tried the diet after loss response to biologics were included. All adult patients included in this study were adults who had failed a previous medical therapy and had asked for dietary treatment, only one of the adult patients (not included in analysis) preferred to try EEN.

All patients who tried the diet, met inclusion exclusion criteria and had available data were included in this study.

CD was confirmed by established criteria based on clinical, radiological, endoscopic and histopathological findings (27,28). Location of disease and disease behavior were defined by macroscopic involvement using the Paris classification (18). Disease activity was defined by a Harvey Bradshaw index for all participants, and a PCDAI without the height component was calculated for those 18 or younger.

All patients receiving the diet were offered an immunomodulator as this standard clinical practice when using EEN in our institution. Concurrent stable dose maintenance therapy with immunomodulators such as thiopurines and methotrexate was allowed, as was initiation of thiopurines at onset of nutritional therapy, as this is standard clinical practice for use of EEN in children, and thiopurines do not induce remission in active disease before the time of our endpoint at 6 weeks. Patients who received concurrent induction of remission agents medications such as steroids, 5ASA, methotrexate or antibiotics were excluded, as were patients who were receiving induction doses of a biological therapy. Patients who were on stable biological therapy who had failed therapy after the first three doses or lost response were included as long as no change in the biologic dose or schedule occurred.

Dietary Intervention: All patients received an identical dietary format, which was used for a period of 6 weeks, and then a step down diet for an additional 6 week period. The first period involved a more restricted diet (abbreviated diet in appendix). All patients received a three page handout with instructions regarding the diet, and preparation of food, including a list of allowed and disallowed foods and products. An explanation regarding the principles was given to all patients by a dietician or one of the physicians. All patients were offered one of two palatable polymeric formulas containing 1 Kcal/ml, either Modulen™ (Nestle, Switzerland) or Pediasure (Abbott, USA) irrespective of age, after tasting the formula, according to preference, with a volume calculated to provide 50% of calories from the formula based on current weight. The use of up to 50% PEN is standard even when medical therapy is used, as is considered a supplemental therapy for nutritional purposes to guarantee a minimum intake of calcium and protein, and ensure growth, which is a significant problem in children with active CD. Specific spices and herbs were also allowed while all other condiments and sauces were not allowed. Specifically, gluten, dairy products, gluten free baked goods and breads, animal fat, processed meats, products containing emulsifiers canned goods and all packaged products with a due date were not allowed. In the second 6 week period formula to supply only 25% of calories was continued, a fixed portion of whole grain bread was allowed as were small amounts of nuts fruits legumes and vegetables. Patients with strictures continued quantitative restriction of fruits and vegetables on an individual basis. Individuals who refused to drink the formula could take the diet without supplementation, however this was discouraged by the team, as the formula was the primary source of calcium. Children were asked to return after 3 weeks to determine response and compliance, and all patients were asked to return after 6 weeks. From 2012 a specific dietary team answered all questions regarding the diet (R.S-B & T. P-G) and offered cooking tips, and from 2013 a hot line was instituted to take calls in addition to office visits.

Diet: as elaborated in Example 2 below.

Endpoints: our primary endpoint was remission on an intention to treat principle after 6 weeks of therapy (defined as PCDAI <7.5 without the height item (29) or a Harvey Bradshaw index ≤3 if the patient was an adult (26). Secondary endpoints were normalization of C reactive protein (CRP) (defined as ≤0.5 mg/dL), response defined as a drop in PCDAI of at least 12.5 points for children or a drop in HBI of at least 2 points, change in standard blood tests from baseline such as hemoglobin, albumin, erythrocyte sedimentation rate (ESR) and C reactive protein (CRP). Patients who had exacerbations or had their therapy switched before the 6 week endpoint were considered failures, and parameters evaluated at 6 weeks were not included in the analysis if they reflected additional added on treatment.

Data analysis: data were stored on spreadsheet and analyzed on SPSS v21 (IBM Inc. USA). Distributions of continuous variables were assessed for normality using the Kolmogorov-Smirnov test (cut-off at p<0.01). Continuous variables with distributions significantly deviating from normal are described as median (min-max), while those with approximately normal distributions so are presented as mean+/−s.d. Continuous variables were compared over time using the t-test for paired samples or the Wilcoxon signed ranks test as appropriate. Dichotomous variables were compared over time using the McNemar test. Additionally, responders were compared to others using the t-test for independent samples or the Mann-Whitney U (as appropriate). Nominal variables were compared by response type using the chi square test, exact as appropriate. All tests are two-sided and considered significant at p<0.05.

Results:

Patient Data

Forty seven patients meeting all inclusion and exclusion criteria (34 children, 13 adults, mean age was 16.1±5.6 years, mean disease duration 2.1±3.4 years, range 6-32 years) were available for analysis. Four patients who were excluded (FIG. 1) since the patient's data from either the baseline or week 6 visit were not available (n=4, 3 remission and 1 failure), and two were excluded because they had received concurrent antibiotics. Baseline data, stratified by age of onset are presented in table 1. Adults did not differ from children with regard to HBI, disease location, baseline acute phase reactants or albumin. Though disease was longer in adults (mean 3.9±4.9 vs. 1.45, ±2.1 years) it was not significant, and there was a non-significant trend for more females in the adult group (p=0.09).

Duration of disease ranged from disease onset to 13 years of disease. In 14 patients, this was the first treatment offered after diagnosis. In all others the treatment was offered because of a relapse or lack of response to a previous therapy. Seven patients relapsed while on PEN as supportive therapy and commenced PEN with CDED. Six patients had strictures with active inflammation, 4 patients had distal ileal strictures (1/3 remission), one had a stricture in the ascending colon (remission) and one had 3 small bowel strictures (remission), all the rest had inflammatory disease (B1). All but three patients included had an elevated CRP or Erythrocyte Sedimentation Rate (ESR) at baseline, the others had elevated fecal calprotectin and a colonoscopy (n=2) or capsule endoscopy (n=1) showing lesions.

TABLE 1

Characteristics of Patients at Baseline

|  | Total cohort (n = 47) | Children (n = 34) | Adults (n = 13) |
|---|---|---|---|
| Baseline | | | |
| Males | 30 (63.4%) | 24 | 6 |
| Age (years) onset | 13.86 ± 4.71 | 11.8 ± 3.1 | 19.3 ± 3.9 |
| Range Age onset | 6-28 | 6-18 | 12-28 |
| Age at baseline diet | 16 ± 5.6 | 13.2 ± 2.6 | 23.4 ± 4.1 |
| Age Range at Diet | 9-31 | 7.5-18 | 18.3-32 |
| Disease duration (yrs) | 2.17 ± 3.53 | 1.45 ± 2.1 | 3.9 ± 4.9 |
| New onset disease | 12 (26%) | 10 (29.5%) | 2 (15.4%) |
| Location (Paris) | | | |
| L1-Ileal/ileocecal | 21 (44.6%) | 16 (47%) | 6 (46.2%) |
| L2-Colon | 3 (6.4%) | 3 (8.8%) | — |
| L3-Ileocolonic | 7 (14.9%) | 5 (14.7%) | 2 (15.4%) |
| L4a-gastric | 1 (2.1%) | 1 (2.9%) | — |
| L4b- Proximal ileum Or jejunum | 2 (4.2%) | 1 (2.9%) | 1 (7.2%) |
| L4a + L1 | 2 (4.2%) | 1 (2.9%) | 1 (7.2%) |
| L4b + L3 | 1 (2.1%) | 1 (2.9%) | — |
| L4b + L1 | 3 (6.3%) | 1 (2.9%) | 2 (15.4%) |
| L4a + L3 | 4 (8.5%) | 4 (11.8%) | — |
| L1 + L4b | 1 (2.1%) | — | 1 (7.2%) |
| Severity | | | |
| Baseline IMM (%) | 26 (55.3%) | 21 (61.8%) | 6 (46.2%) |
| Baseline PCDAI (n = 34) | — | 27.7 ± 9.4 | — |
| Mild (7.5-27.5) | — | 19 (55.8%) | — |
| Moderate (30-37.5) | — | 9 (27.2%) | — |
| Severe (>40) | — | 5 (15.2%) | — |
| HBI baseline | 6.37 + 2.74 | 6.12 ± 2.89 | 6.9 ± 2.17 |
| Remission <4 | 4 (10.6%) | 4 (11.8%) | 1 (7.2%) |
| Mild 4-6 | 21 (44.6%) | 15 (44.1%) | 5 (35.7%) |
| Moderate 7-8 | 12 (25.5%) | 8 (23.6%) | 4 (30.8%) |
| Severe >9 | 10 (21.3%) | 7 (20.6%) | 3 (21.5%) |
| B2- stricture present | 6 (12.7%) | 4 (11.7%) | 2 (15.3%) |
| Baseline CRP (mg/dl) | 3 ± 2.8 | 2.86 ± 2.62 | 2.9 ± 3.32 |
| Baseline ESR | 30.5 ± 17.49 | 31.0 ± 16.6 | 27.9 ± 19.9 |
| Baseline Alb (g/L) | 4.16 ± 1.83 | 4.22 ± 2.03 | 3.98 ± 0.47 |

^-p<0.05^^p<0.01
PCDAI in patients ≤18
CRP, C-reactive protein; ESR, erythrocyte sedimentation rate; and PCDAI, pediatric Crohn's disease activity index; HBI, Harvey Bradshaw Index, IMM, Immunomodulator Response by Week 6

Response was obtained in 37/47 patients (78.7%), and remission in 33/47 patients (70.6%). Among children, full remission was obtained in 18/24 (75%) patients with mild disease, 5/7 (71%) with moderate disease, and 1/3 (33.3%) with severe disease. Table 2 presents data regarding disease activity and severity before and after therapy. Five patients were not compliant (2 did not perform the diet at all as instructed, due to lifestyle, and failed to improve, and 3 complied for the most part but allowed occasional products that were not allowed (2/3 full remission). In addition 7 refused to take any formula but were compliant with the CDED. The rest of the patients used the diet as instructed for the first few weeks unless no improvement was seen, and they were treated with other medications.

Thirty four patients were 18 or younger (remission 24/34, 70.1%), 13 adults were aged 19-32 (9/13 remission, 69.2%), thus remission rates were similar in children and adults. Among new onset patients (n=12), remission was obtained in 6/10 (60%) children, and in 2/2 adults. Among patients with relapses, remission was obtained in 18/24 (75%) children and 7/11 (63.6%) of adults.

Normalization of CRP (CRP ≤0.5 mg/dL) was present in 21/30 patients with previously elevated CRP in remission (70%). Among responders, a CRP <1 mg/dL occurred in 31/34 (90%) responders with a previously elevated CRP. A significant decline (p<0.001) by week 6 was seen for mean PCDAI, HBI, ESR and CRP, while changes in albumin and weight were not statistically significant at this time point, but were significant by week 12. Changes between week 0 and week 6 CRP and PCDAI for individual patients are portrayed in FIGS. 2a and 2b.

Factors Predicting Response at Week 6

The only significant predictor of response was baseline disease severity for children. The mean PCDAI without height component for those entering remission was 26.1±9 vs. 32±9 for failures, p=0.013). Mean HBI for the whole cohort however was not significantly different (table 1). There was no difference between patients obtaining remission and those not obtaining full remission with regard to inflammatory biomarkers or use of an immunomodulator, (61.7%, vs. 60% p=0.66). All but seven patients in response were on a stable dose immunomodulator or biologic or did not receive immunomodulation prior to week 6

Five patients started the diet after failing to achieve remission with a biologic or after loss of response to biologics (infliximab n=3, infliximab+methotrexate n=1, loss of response to both adalimumab and infliximab n=1), of these 3/5 obtained remission with the diet and two failed. Seven patients took the diet without any formula because of intolerance or taste issues, 6/7 obtained remission with the whole food diet alone.

Changes After Week 6

Table 3 portrays pairwise comparisons between week 0 and week 12 for the whole cohort without medication change and with follow up after reintroduction of limited bread and free exposure to fruits vegetables and nuts (unless a stricture was present). Due to abnormal distribution of HBI results, HBI is also portrayed as median with range in table 3. Significant improvement compared to baseline was present for PCDAI and HBI, CRP and ESR as well as weight gain and improvement in albumin.

At week 12, 27/32 (84%) of patients in remission with follow up were still in remission after the step down phase, 28/32 had repeated acute phase reactants. Three patients who relapsed by week 12 performed the first stage diet again, 2/3 regained remission. Two required other therapies.

At present we have data for fifteen patients who have remained on stable therapy without change in medication and practiced dietary restriction, regarding mucosal healing (14 follow up colonoscopy, one MRE+ calprotectin, range 6 months-2 years after treatment). Eleven patients were on an immunomodulator, 4 were on diet alone without medication. Eleven of these 15 patients had complete mucosal healing or normal MRE with normal calprotectin, including the four on diet alone, 3 had active disease and one patient with previous extensive disease had complete healing in most segments but had residually active disease in a strictured segment of bowel.

TABLE 2

Pairwise Comparisons of Parameters Between Baseline and Week 6

| N = 47 | Baseline | Week 6 | P value |
|---|---|---|---|
| HBI | 6.37 ± 2.74 | 1.85 ± 2.93 | 0.000 |
| PCDA1 (n = 34) | 27.7 ± 9.4 | 5.4 ± 7.98 | 0.000 |

TABLE 2-continued

Pairwise Comparisons of Parameters
Between Baseline and Week 6

| N = 47 | Baseline | Week 6 | P value |
|---|---|---|---|
| CRP | 2.9 ± 2.7 | 0.86 ± 1.0 | 0.000 |
| ESR | 29.3 ± 16.6 | 17.0 ± 10.9 | 0.000 |
| Hemoglobin | 12.2 ± 1.3 | 12.3 ± 1.2 | 0.5 |
| Albumin | 4.2 ± 2 | 4.07 ± 0.40 | 0.67 |

Pairwise comparisons only in subjects with parameters at both time points

CRP, C-reactive protein; ESR, erythrocyte sedimentation rate; and PCDAI, pediatric Crohn's disease activity index; HBI, Harvey Bradshaw Index calculated for all patients. PCDAI calculated only for children and adolescents through age 18.

Changes After Week 12:

Table 3 portrays changes between week 0 and week 12 for the whole cohort after reintroduction of limited bread and free exposure to fruits vegetables and nuts (unless a stricture was present).

TABLE 3

Pairwise Comparisons of Parameters
Between Week 0 and Week 12

| N = 36 | Week 0 | Week 12 | P value |
|---|---|---|---|
| HBI (mean) | 5.9 ± 2.7 | 0.75 ± 1.75 | 0.000 |
| HBI (median + range) | 6.0 (0-13) | 0.0 (0-6) | 0.000 |
| PCDAI (n = 24) | 25.7 ± 8.9 | 6.44 ± 8.07 | 0.000 |
| CRP | 2.3 ± 2.3 | 0.81 ± 0.64 | 0.002 |
| ESR | 25.7 ± 12.7 | 17 ± 8.2 | 0.001 |
| Hemoglobin | 12.0 ± 1.4 | 12.6 ± 1.3 | 0.1 |
| Albumin | 3.8 ± 0.42 | 4.12 ± 0.39 | 0.000 |

Pairwise comparisons only in subjects with parameters at both time points

Abnormally distributed variables are present as median values

CRP, C-reactive protein; ESR, erythrocyte sedimentation rate; and PCDAI, pediatric Crohn's disease activity index; HBI Harvey Bradshaw Index (used in all patients) PCDAI calculated only for children and adolescents through age 18

Discussion: exclusive enteral nutrition is very effective for induction of remission in mild to moderate recent onset pediatric CD. The mechanism of action is unknown at present, and the biggest drawback is the difficulty in implementing an exclusive monotonous liquid diet for 6-8 weeks. We have previously proposed that the mechanism may be exclusion of dietary products that may affect intestinal permeability, enhance translocation or adherence of bacteria to epithelium, or promote a pro inflammatory microbiome in animal models and cell lines (12).

We have shown that a dietary intervention in mild to moderate disease, based on 50% PEN and a structured diet that excludes these products can induce clinical remission with a reduction in inflammatory markers. The CD ED, which avoided or reduced exposure to animal fat, dairy products, gluten and emulsifiers and enabled exposure to fiber from fruits led to remission in 66% of patients, primarily in patients with early mild to moderate disease. Furthermore, this diet was accompanied by a significant decrease in CRP and ESR, and normalization of CRP 2/3 of patients entering remission. A previous study has shown that 50% PEN with free diet induced remission only in 15% of patients and did not decrease CRP, so it is likely that the higher remission rates and significant decrease in CRP shown in our study are likely due to the exclusion of dietary factors (17). The diet appeared to be effective even in patients who did not take any supplemental formula (no PEN), as evidenced by the fact that 5/6 patients who just used the CDED without any formula entered full remission. The only patient that failed normalized her ESR and CRP but had persistent mild symptoms.

This is significant since the CDED allows access to specific foods to improve palatability and allowed patients who would have otherwise refused to use nutritional therapy, an alternative to steroids and biologics for induction of remission in mild to moderate disease. Furthermore, in this small cohort, young adults responded just as well as children and adolescents, and this may allow broader use of nutritional therapy in adults.

While we cannot compare head to head efficacy, the remission rate in our study (68%) was slightly lower than the 79% remission rate shown in the multicenter GROWTH CD study (Levine et al, Inflamm. Bowel Dis, in press) and the rates in two recent cohorts which ranged from 75-80% (14,16). In these three cohorts, patients treated were primarily new onset disease, while in our study we included patients with long standing and refractory disease, that tend to fare less well. In fact, almost all the patients two exceptions) who entered full remission had a disease duration <1.5 years. In our study, the majority of patients were not treatment naïve. On the other hand, the majority of the patients in this study had mild disease.

A second difference may be the rigorous criteria for remission we used in children (PCDAI <7.5 without the height component), two children with a PCDAI of 10 at week 6 were not registered as remission using our criteria but may have been considered remission using criteria from previous studies. In addition, the vast majority of our patients were treated from the start as outpatients. In many centers in Europe it is customary to hospitalize the patients until they consume the full amount of formulae, often with nasogastric tubes, which guarantees compliance.

The population investigated was a selective population involving primarily children and very young adults with a relatively short duration of disease, primarily with small bowel involvement (including ileocolonic disease) and primarily patients with mild to moderate luminal disease. These are considered the optimal patients at present for use of EEN based primarily on experience, though EEN has not been investigated properly in other settings such as prolonged disease, severe disease or colonic disease. Buchanan et al. recently evaluated EEN in 110 children and found that EEN was just as effective in isolated colonic disease as in small intestinal disease (14). Within our selected population, disease severity was the only significant predictor of response. The diet succeeded in obtaining remission in 2/4 patients who failed to achieve remission or lost response to biologics, and the response rates were similar in mild and in moderate disease. On the other hand, 4/29 patients had mild relapses after a previous remission by 12 weeks, and all had mild flares. One of these patients reverted to the initial diet and regained remission.

EEN has become the dietary intervention of choice because it allows remission in a high proportion of children without requiring corticosteroids, improves growth and bone mineral density and mucosal healing (13). It is not an easy therapy to use since patients are not allowed to consume any other food for 6-8 weeks.

Research in animal models and cell lines have supplied us with candidates for environmental factors that may allow stimulation of the adaptive immune response by luminal bacteria (12). Bacterial adherence and translocation are inhibited by the mucous layer, the integrity and selective permeability of the epithelium, and bacterial clearance mechanisms. While it is beyond the scope of this discussion to review all the dietary components that may affect the function of the intestinal barrier, it is important to understand that processed or industrialized foods contain combinations of products that may affect the intestines ability to contain bacteria to the lumen. Roberts et al demonstrated that translocation of Adherent Invasive *E coli* (AIEC) across intestinal M Cells and Peyer patches is increased by exposure to low levels of a commonly used emulsifier (polysorbate 80), and that this translocation can be inhibited by soluble fiber (23). This emulsifier is commonly used in ice creams, whipping creams, dessert toppings, condiments and dill pickles. Carboxymethylcellulose (E 466), an emulsifier and thickener commonly used in dairy products, processed cheeses, ice cream, processed meats and breads may allow bacteria to migrate and adhere to the epithelium, possibly by affecting the mucous layer (22). Milk fat and animal fat has been shown to increase IP and alter the microbiome, In a study performed by Devkota et-al (21) three different diets were given to IL 10−/− mice Low Fat, Polyunsaturated Fat (PUFA) and Milk derived Fat. Only mice exposed to the latter diet developed a microbiome that included the colitogenic bacteria *B. wadsworthia*, which was associated with an increase in colitis from 25-30% to 60% in 6 months (21). Martinez et-al (19) compared CEABAC10 mice with or without AIEC to WT mice with or without AIEC, both groups were fed a western diet rich in fats and simple sugars or regular chow. The Western diet promoted mucin degrading bacteria increased AIEC counts and increased intestinal permeability (19). Gliadin from Gluten induces zonulin release in the small intestine, increasing IP in a dose dependent fashion (30). Maltodextrin has been found to promote AIEC biofilms, and increase adhesion of AIEC strains to epithelial cells and macrophages via upregulation of type 1 pili expression (31). Maltodextrin is a thickening and binding agent found in breakfast cereals as well as aspartame and sucralose, commonly used as artificial sweeteners.

Several important implications for therapy and our understanding of upstream events are involved in pathogenesis. The most important implication of the results of our study is that it serves as further support for the concept that EEN may induce remission and a decrease in inflammation primarily by excluding components of Western diet. This also suggests that one or more of these components excluded in our diet plays a role in instigating the inflammatory cascade, or as we have postulated, an acquired bacterial clearance defect, and that there may be a window of opportunity to use this diet early in the disease. The second implication is that we could conceivably intervene with a more palatable and acceptable diet and achieve remission in a high proportion of selected patients, and possibly develop a more evidenced based exit strategy from the initial 6-8 weeks of EEN using a diet that reduces exposure to these products. More importantly perhaps, this may move us a little closer in closing the research gap between humans and animal models in understanding the pathogenesis of the disease.

Researching the association between diet and remission in human subjects may have implications beyond the therapeutic implications. Crohn's disease appears to have a strong environmental component, and identification of dietary factors that might be involved in pathogenesis or trigger inflammation might open new therapeutic strategies for prevention of disease. Though research in animal models has helped identify specific suspects (19-23,31), and allow incorporation of these factors into models for pathogenesis (12,32), only human studies can confirm the role of these components in triggering inflammation.

Example 2

The following diet is used for the first 6 weeks, to gain control of the disease and reduce inflammation. This stage is the most critical, and if it doesn't succeed, the next stages are 0likely to fail. Gaining control and diminishing the inflammation are crucial for the success of this diet over time. The success of any diet depends on the composition and structure of the diet (the science), and adherence. The most successful dietary plan will be unsuccessful if you do not follow the diet. The key to success is positive thinking. If the diet is for your child, spend time prepping for the diet. The phrases "you can do it", "we can beat this" are helpful starter phrases. If you don't believe that they can do it, why should they? Make this a family project by supporting the child, involving them in menu planning and in cooking. Counting down the days until the next stage is less helpful, but can be used during the last two weeks of the first stage. Adult logic doesn't hold much sway with children. Children and adolescents are unlikely to be impressed that "this is healthy", this is good for you" or "this is bad for you".

Spend time planning meals and looking for recipes. Tasty food will overcome the feeling of loss at losing snack foods and junk food.

All the products should be fresh. "Fresh" does not correspond to "organic". Do not buy and frozen foods for the first 12 weeks. However, fresh food such as fresh fish or chicken breast can be frozen.

The first page contains allowed foods. The subsequent pages include the foods that are not allowed for the first 6 weeks. The diet is divided by food groups to keep this simple.

Explanations and Comments

Please perform this diet exactly as instructed. There are numerous foods, spices, fruits and vegetables that are not on this list, and they have been removed for a reason. The success of this diet requires adhering to the diet exactly as written. Products that do not appear in the allowed ingredients list should not be consumed, even if they do not appear in the list of forbidden products.

Allowed foods may be grilled, fried, baked, boiled, or broiled. Foods that are marked with an asterisk (eggs, meat, potatoes and bananas), should be consumed every day in the quantities registered.

This phase does not include any dairy products and limited calcium. Children should receive 50% of their recommended calories from a medical polymeric formula containing 1 kcal/m"1. Examples include Modulen or Pediasure. Adults may consume these formulas as well, or might use the diet without any supplementation by a liquid formula. If this is the case, please consult your physician or dietician about calcium supplements. Concentrated formulas that contain 1.5 kcal/m"1 are discouraged.

Do not believe labels, certain components that are believed to be harmful may not be registered, or may appear under a more palatable label. For instance, some emulsifiers may appear as "dietary fiber". This diet has no connection to organic or non-organically produced foods. Organic foods that are not on this list may be counterproductive.

It is important to organize meals and produce. The success requires variety in cooking. Since the list of ingredients is limited, it is best to have them always available. Stock up on fresh herbs and olive oil. You may pay more for premium olive oil, but you will save on the beverages, junk food and meat bills.

Cooked food may be frozen. We recommend cooking in quantities that allow left overs to be consumed at a later time.

You can prepare home-made tomato sauce from fresh tomatoes, olive oil, spices and herbs. Home-made mayonnaise is also acceptable.

Modulen or vanilla flavored liquid formulas can be blended with fresh bananas or strawberries to add taste and variety. Cinnamon may be added as well.

If you intend to eat in restaurants, freshly grilled fish, chicken breast, rice and baked potatoes are the safest foods. Fried eggs or hard boiled eggs are also safe. Scrambled eggs may be made from mixes or contain dairy products. Restaurants will most likely use prepared sauces, mixes, dressings that are not allowed. Mashed potatoes may be ordered as long as they are mashed from potatoes, without added dairy products. Frozen potatoes (used for fries in most restaurants) and ready mixes will likely contain preservatives, sulfites, and thickeners. Make sure that butter and dairy products are not added to meats, fish and potatoes.

Crohn's Disease Exclusion Diet Week 1-6 Weeks
Allowed Foods
Meat/Protein

*Fresh chicken breast or fresh fish (no seafood)—unlimited quantities. Patients should have one or the other at least once daily, but can consume these more than once a day. (Smoked, canned, precooked or processed chicken breast or fish are not allowed).

Fresh Unprocessed beef lean steak (lean meat such as sirloin)—may be consumed up to once a week (up to 200 grams) from week 4. Pre-prepared ground beef is not allowed, but lean steak can be ground by the butcher or at home in to ground beef without additives. Beef is optional, and cannot replace chicken or fish.

*2 Eggs day (all patients should consume 2 eggs/day)
Carbohydrates
  White Rice (unlimited quantities)
  Rice Noodles without preservatives (one portion per day)
  *2 fresh Potatoes (peeled). Frozen potatoes are not allowed. Only one potato can be consumed at any given meal. 8 baby potatoes can be used as an alternative.
Fresh Fruits and Vegetables
  2 tomatoes, or 6 cherry tomatoes, 2 cucumbers (peeled), 1 carrot if no stricture is present. If a stricture is present carrot shavings are allowed, fresh spinach (1 cup uncooked leaves), 1 apple (peeled—if no tight stricture), *2 bananas (please consume 2 bananas/day), 1 avocado (the avocado should not be consumed all at once, and may be consumed over two meals), 5 strawberries, 1 slice melon
Allowed Condiments for Cooking:
  Olive oil (unlimited), canola oil (unlimited), salt, pepper, paprika, cinnamon stick fresh herb leaves (mint leaves, oregano, coriander, rosemary, sage, basil, thyme, parsley, dill. remove stalks if they are going to be eaten, stalks may remain if used just for cooking.), fresh onion, garlic and ginger, fresh carrot shavings for salad, rice or soup, true honey for cooking (do not consume too frequently, we recommend up to 3 tablespoons a day), table sugar (3 teaspoons day for cooking or tea), fresh lemons for juice or zest
Beverages
  Water, Soda, herbal teas prepared from fresh leaves (please note that slices of lemon, lime, orange or mint leaves may be added for taste)
  One glass of freshly squeezed orange juice daily (not from cartons or bottles)
Forbidden Foods and Ingredients
  Dairy products of any kind, margarine, wheat, breakfast cereals, breads and baked goods of any kind, yeast for baking, granola, power bars or granola bars, gluten free products not listed above, soy products, potato or corn flour, corn, frozen vegetables, frozen fruits, processed or smoked meats and fish (sausages, luncheon meats, salamis, fish sticks), sauces, salad dressings, syrups and jams of any kind (mayonnaise, ketchup, mustard, thousand island dressing, chile sauce, tabasco, steak sauce, curry sauce, tomato paste, canned products and dried fruits, packaged snacks (potato chips, pretzels, popcorn, nuts etc), all soft drinks, fruit juices and sweetened beverages, vitamin waters, wines, beers, alcoholic beverages, coffee, frozen drinks, smoothies at restaurants or stores, candies, chocolates, cakes, cookies and chewing gum, artificial sweeteners, vinegars, mixed spices, curry or tomato pastes, nuts.

Crohn's Disease Exclusion Diet Week 7-12 Weeks
Allowed Foods
Meat/Protein
  Like in weeks 1-6 with the addition of one small can of Tuna (packed in oil) twice a week
Carbohydrates
  Like in weeks 1-6 with the addition of:
  From week 8 one slice whole grain bread
Quinoa
Vegetables
  Like in weeks 1-6 with the addition of: 1 cup Lettuce, ½ red bell pepper, 4 fresh mushrooms, 1 zucchini, 2 small pieces of broccoli. From week 8 additional vegetables such as beets, squash, cabbage, cauliflower can be gradually added as substitutes for the new vegetables mentioned above.
Fruit
  Like in weeks 1-6 with the addition of exchanges (1 pear, nectarine, kiwi, or peach instead of apple, blueberries instead of strawberries), continue to consume 2 bananas per day
  Legumes: (lentils, dry chickpeas), Canned legumes are not allowed.
  Nuts: 6 whole Almonds (unsalted unprocessed) or 6 walnut halves (unsalted unprocessed).
Allowed Condiments for Cooking:
  Like in weeks 1-6 with the addition of fresh carrot shavings for salad, rice or soup
Beverages
  Like in weeks 1-6.
Forbidden Foods and Ingredients
  Like in weeks 1-6.

Reference is now made to FIG. 1A which shows changes in 45 patients in HBI (Harvey Bradshaw Index) from the beginning of the diet and after 6 weeks of preforming the diet. Diamonds represent HBI score at the beginning of the diet while square represent HBI score after 6 weeks of diet. The Y axis represent the HBI score and each scale mark on the X axis represent a patient following the diet described in Example 2. It is clear from the graph that after 6 weeks of diet all patients received an HBI score lower than 5 which indicates remission. Most patients received a score of 0.

Figure 1B:
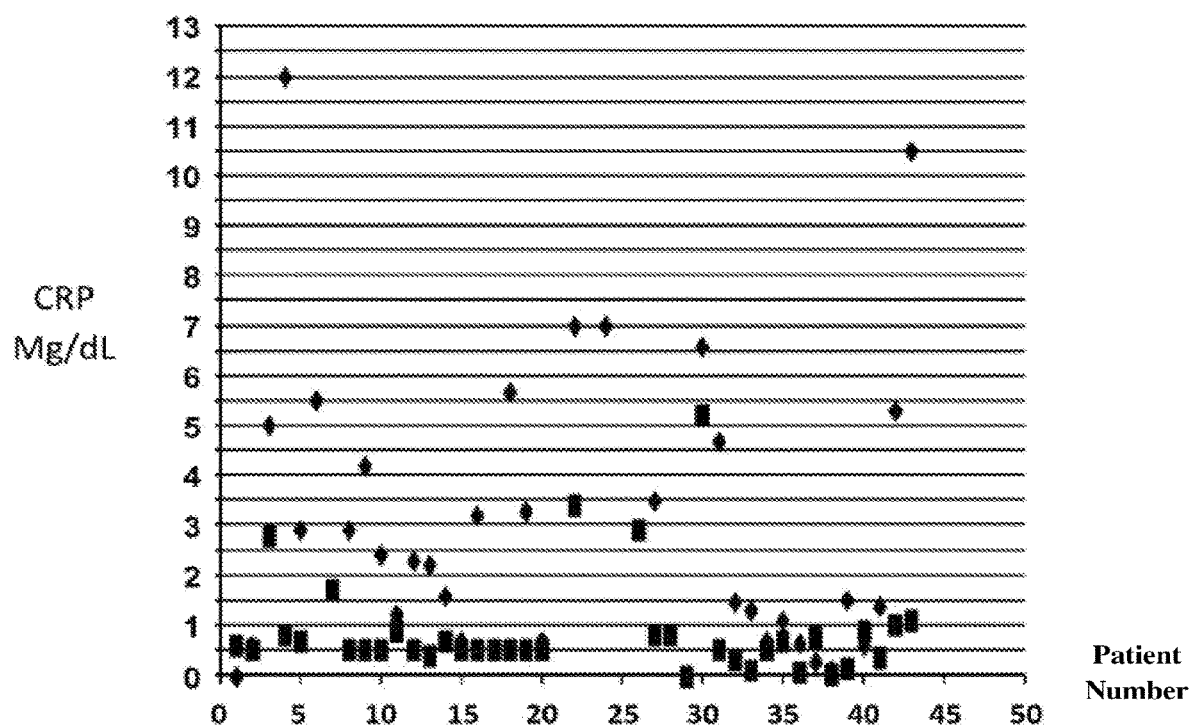
FIG. 1B shows changes in 45 patients in CRP from the beginning of the diet and after 6 weeks of preforming the diet.

Reference is now made to FIG. 1B which shows changes in 45 patients in CRP from the beginning of the diet and after 6 weeks of preforming the diet. Elevated CRP is indicative of inflammation. Diamonds represent CRP levels at the beginning of the diet while square represent CRP levels after 6 weeks of diet. It is clear from the graph that after 6 weeks of diet the CRP levels of most patients dropped to below 1.

Figure 2:
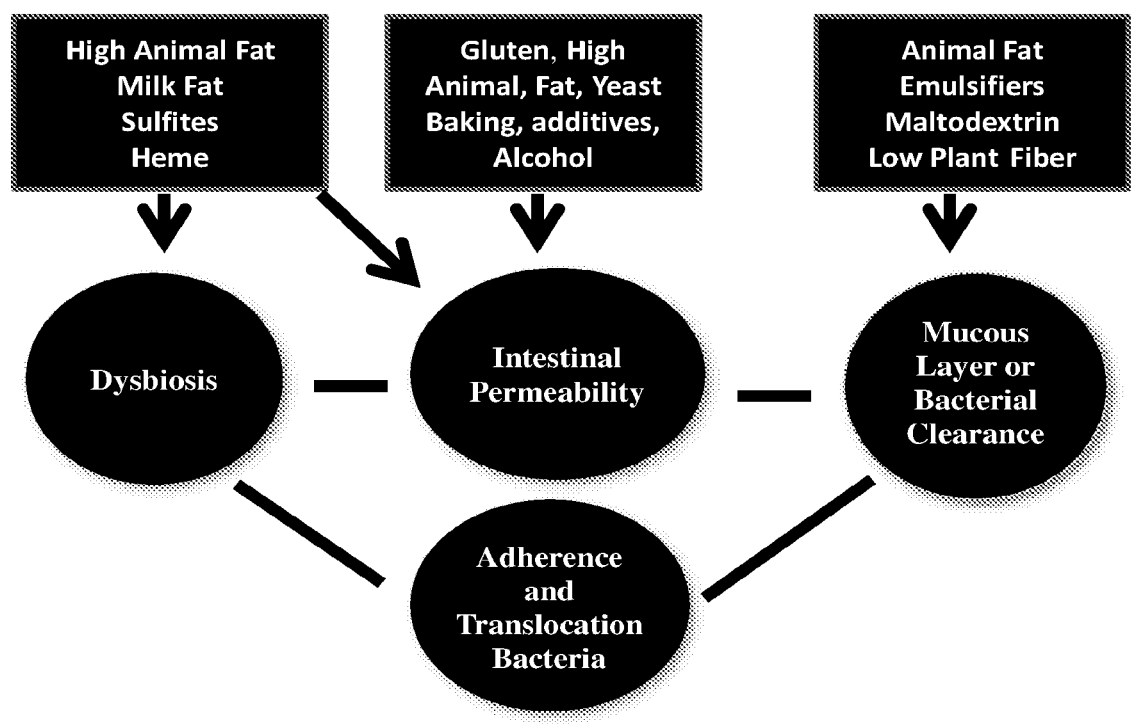
FIG. 2 is an illustration of disallowed foods in CDED and criteria for disqualification.

Reference is now made to FIG. 2 which is an illustration of disallowed foods in CDED and criteria for disqualification.

REFERENCES

1. Kaser A, Blumberg R S. Autophagy, microbial sensing, endoplasmic reticulum stress, and epithelial function in inflammatory bowel disease. Gastroenterology 2011 May; 140:1738-47.
2. Sartor B. Microbial Influences in Inflammatory Bowel Diseases. Gastroenterol 2008; 134:577-94
3. Manichanh C, Borruel N, Casellas F et-al. The gut microbiota in IBD. Gastroenterol. Hepatol 2012; 9: 599-608
4. Bernstein C N, Rawsthorne P, Cheang M, et al. A population-based case control study of potential risk factors for IBD. Am J Gastroenterol. 2006; 101:993-1002
5. Muegge B D, Kuczynski J, Knights D, et al. Diet drives convergence in gut microbiome functions across mammalian phylogeny and within humans. Science. 2011; 332:970-974.
6. De Filippo C, Cavalieri D, Di Paola M, et al. Impact of diet in shaping gut microbiota revealed by a comparative study in children from Europe and rural Africa. Proc Natl Acad Sci USA. 2010; 107:14691-14696.
7. Kajiura T, Takeda T, Sakata S, et al. Change of intestinal microbiota with elemental diet and its impact on therapeutic effects in a murine model of chronic colitis. Dig Dis Sci. 2009; 54:1892-1900.
8. Martin H M, Campbell B J, Hart C A, et al Enhanced *Escherichia coli* adherence and invasion in Crohn's disease and colon cancer. Gastroenterology. 2004; 127:80-93
9. Ryan P, Kelly R G, Lee G, et al. Bacterial DNA within granulomas of patients with Crohn's disease—detection by laser capture microdissection and PCR. Am J Gastroenterol. 2004; 99:1539-1543.
10. Qiurong L, Wan C, Tan C et-al Molecular phylogenetic characterization of the microbiota in ulcerated and non ulcerated regions in the patients with Crohn's diseas. PLoS ONE 7(4): e34939. doi:10.1371/journal.pone.0034939.
11. Willing B, Dicksved J, Halfvarson J et-al. A pyrosequencing study in twins shows that the gastrointestinal microbial profiles vary with inflammatory bowel disease phenotypes. Gastroenterol 2010; 139:1844-1854.
12. Levine A, Wine E. Effects of enteral nutrition on Crohn disease: Clues to the impact of diet on disease pathogenesis. Inflamm Bowel Dis 2013; 19:1322-9.
13. Grover Z, Muir R, Lewindon P. Exclusive enteral nutrition induces early clinical, mucosal and transmural remission in paediatric Crohn's disease. J Gastroenterol 2013; DOI 10.1007/s00535-013-081.5-0.
14. Buchanan E, Gaunt W, Cardigan T et-al. The use of exclusive enteral nutrition for induction of remission in children with Crohn's disease demonstrates that disease phenotype does not influence clinical remission. Aliment Pharmacol Ther 2009; 30: 501-50.
15. Yamamoto T, Nakahigashi M, Umegae S et-al. Impact of long-term enteral nutrition on clinical and endoscopic recurrence after resection for Crohn's disease: a prospective, non-randomized, parallel, controlled study. Aliment Pharmacol Ther 2006; 25:67-72.
16. Rubio A, Pigneur B, Garnier-Lengline'H et-al. The efficacy of exclusive nutritional therapy in paediatric Crohn's disease, comparing fractionated oral vs. continuous enteral feeding. Aliment Pharmacol Ther 2011; 33: 1332-1339.
17. Johnson T, Macdonald S, Hill S et-al. Treatment of active Crohn's disease in children using partial enteral nutrition with liquid formula a randomised controlled trial. Gut 2006; 55:356-361.
18. Chapman-Kiddell C, Davies P, Gillen L et-al. Role of Diet in the Development of Inflammatory Bowel Disease. Inflamm Bowel Dis 2010; 16:137-151.
19. Martinez M, Denizot J, Dreux N et-al. Western diet induces dysbiosis with increased *E coli* in CEABAC10 mice, alters host barrier function favouring AIEC colonization. 2013; doi:10.1136/gutjnl-2012-304119.
20. Suzuki T, Hara H. Dietary fat and bile juice, but not obesity, are responsible for the increase in small intestinal permeability induced through the suppression of tight junction protein expression in LETO and OLETF rats. Nutr Metab 2010; 7:19.
21. Devkota S, Wang Y, Musch M et-al. Dietary-fat-induced taurocholic acid promotes pathobiont expansion and colitis in IL10−/− mice. Nature 2012; 487: 104-9.
22. Swidsinski A, Ung V, Sydora B et-al. Bacterial overgrowth and inflammation of small intestine after Carboxymethylcellulose ingestion in genetically susceptible mice. Inflamm Bowel Dis 2009; 15:359-364.
23. Roberts C, Keita A, Duncan S et-al. Translocation of Crohn's disease *Escherichia coli* across M-cells contrasting effects of soluble plant fibres and emulsifier. Gut 2010; 59:1331-1339
24. Ekbom A. Appendicectomy and childhood hygiene: different sides of the same coin? Gut. 1998; 43:451.
25. Hyams J S, Ferry G D, Mandel F S, Gryboski J D, Kibort P M, Kirschner B S, Griffiths A M, Katz A J, Grand R J, Boyle J T, et al. Development and validation of a paediatric Crohn's disease activity index. J Pediatr Gastroenterol Nutr. 1991 May; 12:439-47.
26. Harvey R F, Bradshaw J M. A simple index of Crohn's-disease activity. Lancet. 1980 8; 1:514
27. Levine A, Griffiths A M, Markowitz J, Wilson D C, Turner D, Russell R K, Fell J, Ruemmele F M, Walters T, Sherlock M, Dubinsky M, Hyams J S. Paediatric Modification of the Montreal Classification for Inflammatory Bowel Disease—the Paris Classification. Inflamm Bowel Dis 2011; 17:1314-21
28. Porto Criteria—The ESPGHAN Revised Porto Criteria for the Diagnosis of Inflammatory Bowel Disease in Children and Adolescents . . . J Pediatr Gastroenterol Nutr
29. Turner D, Griffiths A M, Walters T D, Seah T, Markowitz J, Pfefferkorn M, Keljo D, Otley A, Leleiko N S, Mack D, Hyams J, Levine A. Appraisal of the paediatric Crohn's disease activity index on four prospectively collected datasets: recommended cutoff values and clinimetric properties. Am J Gastroenterol. 2010; 105:2085-92
30. Lammers K, Lu R, Brownley J et-al. Gliadin induces an increase in intestinal permeability and zonulin release by binding to the chemokine receptor CXCR3. Gastroenterol 2008; 135: 194-204.
31. Nickerson K P, McDonald C. Crohn's Disease-Associated Adherent-Invasive *Escherichia coli* Adhesion Is Enhanced by Exposure to the Ubiquitous Dietary Polysaccharide Maltodextrin. PLOS One 2012; 7: e52132. doi:10.1371

32. Roberts C L, Rushworth S L, Richman E, Rhodes J M., Hypothesis: Increased consumption of emulsifiers as an explanation for the rising incidence of Crohn's disease. Journal of Crohn's and Colitis 2013 7, 338-341.

The invention claimed is:

1. A method for providing a diet for a Crohn's disease patient, wherein the patient has active Crohn's disease, the method comprising:

the Crohn's disease patient consuming a first plurality of food products each day for a first time period, the first time period comprising six consecutive weeks, the first plurality of food products comprising per day: a) two eggs, two peeled potatoes, two bananas and at least one portion of fresh chicken breast or fresh fish; b) unlimited amounts of products selected from the group consisting of: white rice, olive oil, canola oil, salt, pepper, paprika, cinnamon stick, fresh herb leaves, fresh onion, fresh garlic, fresh ginger, fresh lemon, water, soda, and herbal teas prepared from fresh leaves; and c) not more than the specified amount for the following products: one portion of rice noodles without preservatives, 3 tablespoons of honey, 3 teaspoons of sugar; 2 tomatoes, 2 peeled cucumbers, 1 cup fresh spinach, 1 avocado, 5 Strawberries, 1 slice melon, and one glass of freshly squeezed orange juice; and the Crohn's disease patient consuming a second plurality of food products each day for a second time period, the second time period begins at completion of the first time period and comprises another six consecutive weeks, the second plurality of food products comprising per day: a) two eggs, two peeled potatoes, two bananas and at least one portion of fresh chicken breast or fresh fish; b) unlimited amounts of products selected from the group consisting of: white rice, olive oil, canola oil, salt, pepper, paprika, cinnamon stick, fresh herb leaves, fresh onion, fresh garlic, fresh ginger, fresh lemon, water, soda, and herbal teas prepared from fresh leaves, and quinoa; c) not more than the specified amount for the following products: one portion of rice noodles without preservatives, 3 tablespoons of honey, 3 teaspoons of sugar; 2 tomatoes, 2 peeled cucumbers, 1 cup fresh spinach, 1 avocado, 5 Strawberries, 1 Slice Melon, one cup of fresh lettuce, ½ red bell pepper, 4 fresh mushrooms, 1 zucchini, 2 small pieces of broccoli, 6 whole almonds or 6 walnut halves, and a ½ cup of dried chickpeas or lentils, wherein the first plurality of food products and the second plurality of food products are fresh, wherein the method further comprises the Crohn's disease patient consuming enteral nutrition in an amount that provides about 50% of daily caloric intake consumed in the first time period and about 25% of the daily caloric intake consumed in the second time period.

2. The method of claim 1, wherein the patient is suffering from mild to moderate Crohn's disease.

3. The method of claim 1, wherein the first and second time periods have at least one feature selected from the group consisting of:

a. the fresh herb leaves are selected from the group consisting of mint leaves, oregano, rosemary, sage, basil, thyme, parsley, dill, and any combination thereof;
b. the almonds or walnuts are unsalted and unprocessed;
c. the avocado is consumed over at least two meals;
d. the 2 peeled potatoes are consumed over at least two meals;
e. the food products are processed in a manner selected from the group consisting of grilling, frying, baking, boiling, broiling, and any combination thereof;
f. after the first time period, the Crohn's disease patient has (i) a pediatric Crohn's disease activity index (PCDAI), as calculated without a height component, that is less than 7.5 for the Crohn's disease patient who is a child or young adult or (ii) a Harvey Bradshaw index (HBI) that is less than 3 for the Crohn's disease patient who is an adult;
g. after the first and second time periods, the Crohn's disease patient has a PCDAI drop of at least about 12.5 points for the Crohn's disease patient who is a child or young adult or a HBI drop of at least 2 points for the Crohn's disease patient who is an adult, relative to the beginning of the first time period; and
h. each of the first and second time periods comprises not consuming the following foods: dairy products of any kind, margarine, wheat, breakfast cereals, breads, baked goods of any kind, yeast for baking, granola, power bars, granola bars, gluten free products, soy products, potato flour, corn flour, corn, frozen vegetables, frozen fruits, processed meats, smoked meats, processed fish, smoked fish, sauces, salad dressings, syrups and jams of any kind, tomato paste, canned products, dried fruits, packaged snacks, soft drinks, fruit juices, sweetened beverages, vitamin waters, alcoholic beverages, coffee, frozen drinks, candy, chocolate, cake, cookies, chewing gum, artificial sweeteners, vinegar, mixed spices, curry, and nuts.

4. The method of claim 1, wherein at least one of the first plurality of food products or the second plurality of food products further comprise additional products if the patient has no strictures; the additional products selected from the group consisting of: no more than 1 peeled apple, no more than 1 carrot; further wherein the no more than 1 peeled apple can be replaced in the second plurality of food products with a fruit selected from the group consisting of no more than 1 pear, no more than one nectarine, no more than one kiwi, no more than one peach, and any combination thereof.

5. The method of claim 1, wherein the first plurality of food products additionally comprise no more than 200 g of unprocessed beef lean steak per week from week 4 through week 6.

6. The method of claim 1, wherein the second plurality of food products additionally comprises at least one selected from the group consisting of: a. no more than 200 g of unprocessed beef lean steak per week; b. no more than 1 slice of whole grain bread from week 8 and onwards; c. no more than a small can of tuna packed in oil up to twice a week; and d. any combination thereof;

further wherein the vegetables in the second plurality of food products are gradually replaced with other vegetables from week 8; the other vegetables are selected from the group consisting of: beets, squash, cabbage, cauliflower, and any combination thereof.

7. The method of claim 1, wherein the patient is a pediatric patient and wherein active Crohn's disease is defined as a Pediatric Crohn's Disease Activity Index (PCDAI) of ≥10.

8. The method of claim 1, wherein active Crohn's disease is defined as a Crohn's Disease Activity Index (CDAI) ≥150.

* * * * *